United States Patent
Okamoto et al.

(10) Patent No.: US 10,388,953 B2
(45) Date of Patent: Aug. 20, 2019

(54) POSITIVE ELECTRODE ACTIVE MATERIAL FOR NONAQUEOUS ELECTROLYTE SECONDARY BATTERY, METHOD FOR PRODUCING SAME, AND NONAQUEOUS ELECTROLYTE SECONDARY BATTERY

(71) Applicant: SUMITOMO METAL MINING CO., LTD., Tokyo (JP)

(72) Inventors: Ryosuke Okamoto, Ichikawa (JP); Kazuhiko Okubo, Ichikawa (JP)

(73) Assignee: Sumitomo Metal Minig Co., Ltd., Tokyo (JP)

( * ) Notice: Subject to any disclaimer, the term of this patent is extended or adjusted under 35 U.S.C. 154(b) by 157 days.

(21) Appl. No.: 15/531,656

(22) PCT Filed: Nov. 27, 2015

(86) PCT No.: PCT/JP2015/083503
§ 371 (c)(1),
(2) Date: May 30, 2017

(87) PCT Pub. No.: WO2016/084966
PCT Pub. Date: Jun. 2, 2016

(65) Prior Publication Data
US 2017/0331107 A1 Nov. 16, 2017

(30) Foreign Application Priority Data

Nov. 28, 2014 (JP) .................................. 2014-240988
Jun. 12, 2015 (JP) .................................. 2015-119696

(51) Int. Cl.
*H01M 4/58* (2010.01)
*H01M 4/131* (2010.01)
(Continued)

(52) U.S. Cl.
CPC .............. *H01M 4/58* (2013.01); *C01G 53/00* (2013.01); *H01M 4/131* (2013.01); *H01M 4/36* (2013.01);
(Continued)

(58) Field of Classification Search
CPC ..... H01M 4/58; H01M 4/131; H01M 10/0525
See application file for complete search history.

(56) References Cited

U.S. PATENT DOCUMENTS

2009/0081546 A1* 3/2009 Ogasawara ........... H01M 4/483
429/218.1
2011/0111289 A1* 5/2011 Choi ..................... H01M 4/131
429/207

(Continued)

FOREIGN PATENT DOCUMENTS

JP 2006-12426 1/2006
JP 2010-92706 4/2010
(Continued)

OTHER PUBLICATIONS

Machine Translation of: JP 2012-195198 A, Yokoyama, Oct. 11, 2012.*

(Continued)

*Primary Examiner* — Kenneth J Douyette
(74) *Attorney, Agent, or Firm* — Gerald E. Hespos; Michael J. Porco; Matthew T. Hespos

(57) ABSTRACT

Provided are a lithium-manganese-nickel composite oxide carrying an organic phosphate with a high capacity and a high cycle characteristic when used as a positive electrode active material of a secondary battery, a method for producing the same, and also a nonaqueous electrolyte secondary battery using the lithium-manganese-nickel composite oxide as a positive electrode active material. The positive electrode active material for a nonaqueous electrolyte secondary bat- (Continued)

tery, wherein an organic phosphite compound or an organic phosphate compound having an organic functional group composed of an alkyl group, an aryl group, and the like adheres to a part or the entire of a particle surface of the lithium-manganese-nickel composite oxide represented by general formula: $Li_tMn_{2-x-y}Ni_xM_yO_4$ (wherein $0.96 < t \leq 1.25$, $0.40 \leq x \leq 0.60$, $0 \leq y \leq 0.20$, and M represents at least one element selected from Mg, Al, Si, Ti, Cr, Fe, Co, Cu and Zn).

16 Claims, 2 Drawing Sheets

(51) Int. Cl.
| | |
|---|---|
| H01M 10/0525 | (2010.01) |
| C01G 53/00 | (2006.01) |
| H01M 4/36 | (2006.01) |
| H01M 4/505 | (2010.01) |
| H01M 4/525 | (2010.01) |
| C01B 25/40 | (2006.01) |
| C07F 9/09 | (2006.01) |
| C07F 9/141 | (2006.01) |

(52) U.S. Cl.
CPC .......... *H01M 4/366* (2013.01); *H01M 4/505* (2013.01); *H01M 4/525* (2013.01); *H01M 10/0525* (2013.01); *C01B 25/40* (2013.01); *C07F 9/09* (2013.01); *C07F 9/141* (2013.01)

(56) References Cited

U.S. PATENT DOCUMENTS

| 2011/0217574 | A1 | 9/2011 | Toyama et al. | |
|---|---|---|---|---|
| 2011/0223469 | A1* | 9/2011 | Matsumoto | H01M 4/131 429/163 |
| 2012/0321911 | A1* | 12/2012 | Watanabe | C01G 51/42 429/5 |

FOREIGN PATENT DOCUMENTS

| JP | 4683527 | 2/2011 |
|---|---|---|
| JP | 2012-195198 | 10/2012 |
| JP | 5149927 | 12/2012 |
| JP | 2013-118068 | 6/2013 |
| JP | 5303081 | 6/2013 |

OTHER PUBLICATIONS

Machine Translation of: JP 2006-012426 A, Sakamoto, Jan. 12, 2006.*
International Search Report dated Feb. 23, 2016.

* cited by examiner

POSITIVE ELECTRODE ACTIVE MATERIAL FOR NONAQUEOUS ELECTROLYTE SECONDARY BATTERY, METHOD FOR PRODUCING SAME, AND NONAQUEOUS ELECTROLYTE SECONDARY BATTERY

BACKGROUND

1. Field of the Invention

The present invention relates to a positive electrode active material for a nonaqueous electrolyte secondary battery, composed of a lithium-manganese-nickel composite oxide that carries an organic phosphite compound or an organic phosphate compound, as well as a method for producing the positive electrode active material.

2. Description of the Related Art

The present invention also relates to a nonaqueous electrolyte secondary battery in which the positive electrode active material for a nonaqueous electrolyte secondary battery is used.

In recent years, a small-sized and light secondary battery having a high energy density has been increasingly demanded along with the popularization of mobile electronic equipment such as a mobile phone and a laptop computer. In addition, a high-power secondary battery has been strongly demanded to be developed as a power source for electric cars including hybrid cars.

Examples of a secondary battery satisfying such demands include a lithium ion secondary battery which is one of nonaqueous electrolyte secondary cells. The lithium ion secondary battery is configured from a negative electrode, a positive electrode, an electrolytic solution, and the like, and a material capable of desorbing and inserting lithium is used as an active material for use in the material of each of the negative electrode and the positive electrode.

Such a lithium ion secondary battery is now actively researched and developed. In particular, a lithium ion secondary battery in which a lithium metal composite oxide is used as a positive electrode material is being increasingly in practical use as a battery having a high energy density, because of exhibiting a 4-V grade voltage.

Specifically, there have been proposed lithium composite oxide particles such as a lithium-cobalt composite oxide ($LiCoO_2$) particle that is relatively easily synthesized, a lithium-nickel composite oxide ($LiNiO_2$) particle in which nickel that is more inexpensive than cobalt is used, a lithium-nickel-cobalt-manganese composite oxide ($LiNi_{1/3}Co_{1/3}Mn_{1/3}O_2$) particle, a lithium-manganese composite oxide ($LiMn_2O_4$) particle in which manganese is used, and a lithium-nickel-manganese composite oxide ($LiNi_{0.5}Mn_{0.5}O_2$) particle.

Among them, a lithium-manganese composite oxide particle having a spinel type crystal structure that can provide a secondary battery excellent in heat stability without cobalt small in the amount of deposit, particularly a lithium-manganese-nickel composite oxide ($LiMn_{1.5}Ni_{0.5}O_4$) particle having a structure where manganese is partially replaced with Ni, has recently attracted attention as a high-energy density material that can exhibit an operating voltage of 4.5 V or more.

Such a spinel type positive electrode active material, however, has the problem of reduction in the battery capacity due to repetition of charging/discharging, namely, the problem of causing a poor cycle characteristic.

One reason for such reduction in the battery capacity is considered to be decomposition of an electrolytic solution in charging, such decomposition being an inherent problem for a high-potential, lithium-manganese-nickel composite oxide. That is, such reduction in the battery capacity is considered to be caused as follows: decomposition of an electrolytic solution is an irreversible reaction and therefore charging/discharging is repeated to thereby cause an electrolytic solution serving as a lithium ion carrier between a positive electrode and a negative electrode to be gradually decreased, resulting in such reduction in the battery capacity. Such an electrolytic solution decomposed here may act as a source of a gas containing hydrogen as a main component, thereby causing any failure such as swelling of a secondary battery.

One reason for such reduction in the battery capacity is also considered to be elution of manganese into an electrolytic solution in charging/discharging, while such elution is not an inherent problem for a high-potential, lithium-manganese-nickel composite oxide. In particular, when a carbon-based material is used in a negative electrode, such reduction in the battery capacity is considered to be caused by precipitation of manganese eluted from a positive electrode onto the negative electrode and thus inhibition of a battery reaction on the negative electrode.

All of such phenomena are caused by a side reaction occurring at the interface between the positive electrode active material and the electrolytic solution. Therefore, in order to improve the cycle of a secondary battery in which a high-potential lithium-manganese composite oxide is used as the positive electrode active material, it is important to control the surface state of the lithium-manganese composite oxide.

For example, Japanese Patent No. 4683527 has reported the following: the particle surface of a spinel type lithium-manganese-nickel composite oxide is coated with at least one metal oxide selected from MgO, $\gamma$-$Al_2O_3$, $TiO_2$, $ZrO_2$ and ZnO, thereby enhancing cycle characteristic.

In Japanese Patent No. 4683527, however, a method is adopted which includes dry mixing a fine particle of the metal oxide for use in coating and a particle of the lithium-manganese-nickel composite oxide and allowing the resulting mixture to adhere to the particle surface of the lithium-manganese-nickel composite oxide, and therefore, such coating is easily ununiform not to achieve a sufficient effect of enhancing cycle characteristic.

In addition, has proposed coating of the surface of lithium-manganese composite oxide with an oxide including a metal element selected from the group consisting of Mg, Al and Cu, and $Li_3PO_4$.

In Japanese Patent No. 5149927, however, the lithium-manganese composite oxide is dispersed in an aqueous solution in the course of a coating process. When the lithium-manganese composite oxide contacts with water, a lithium ion and a hydrogen ion are exchanged with each other in the immediate vicinity of the surface, thereby probably deteriorating input-output characteristics of the material.

Furthermore, Japanese Patent No. 5303081 has proposed addition of a phosphonate compound for the purpose of enhancement in the cycle characteristic of lithium-manganese-nickel oxide.

The phosphonate compound, however, is low in reactivity, and the phosphonate compound is thus required to be added in an amount twice or more per the specific surface area in order to inhibit a metal ion from being eluted, and therefore acts as a resistance to a battery reaction and also reduces the battery capacity.

While such various surface treatment techniques have been thus proposed, it has been difficult to actually enhance cycle characteristic with the capacity of a battery being kept.

An object of the present invention is to provide a lithium-manganese-nickel composite oxide that carries an organic phosphate and that imparts a high capacity and a high cycle characteristic when used as a positive electrode active material of a secondary battery.

Another object of the present invention is to provide a producing method that can easily provide such a lithium-manganese-nickel composite oxide in production on an industrial scale.

Still another object of the present invention is to provide a nonaqueous electrolyte secondary battery in which the lithium-manganese-nickel composite oxide that carries an organic phosphate is used as a positive electrode active material.

SUMMARY

The first aspect of the present invention relates to a positive electrode active material for a nonaqueous electrolyte secondary battery, wherein one or both of an organic phosphite compound represented by the following chemical formula (1) and an organic phosphate compound represented by the following chemical formula (2) adhere(s) to a part or the entire of a particle surface of a lithium-manganese-nickel composite oxide represented by general formula: $Li_tMn_{2-x-y}Ni_xM_yO_4$ (wherein $0.96 < t \leq 1.25$, $0.40 \leq x \leq 0.60$, $0 \leq y \leq 0.20$, and M represents at least one element selected from Mg, Al, Si, Ti, Cr, Fe, Co, Cu and Zn).

[Formula 1]

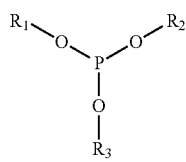

(1)

wherein $R_1$, $R_2$ and $R_3$ each represent an organic functional group including an alkyl group, an aryl group

[Formula 2]

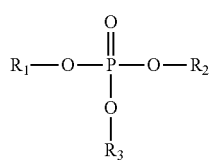

(2)

wherein $R_1$, $R_2$ and $R_3$ each represent an organic functional group including an alkyl group, an aryl group The second aspect of the present invention relates to the positive electrode active material for a nonaqueous electrolyte secondary battery according to the first aspect, wherein a part or the entire of the organic phosphite compound or the organic phosphate compound chemically changed after adhesion of the organic phosphite compound or the organic phosphate compound is chemically bound to a component of the positive electrode active material in the form of a phosphate diester compound represented by the following chemical formula (3) or a phosphonate monoester compound represented by the following chemical formula (4).

[Formula 3]

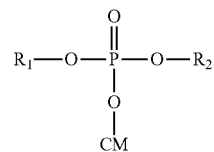

(3)

wherein $R_1$ and $R_2$ each represent an organic functional group including an alkyl group, an aryl group
(CM represents an element constituting the positive electrode active material)

[Formula 4]

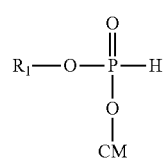

(4)

wherein $R_1$ represents an organic functional group including an alkyl group, an aryl group
(CM represents an element constituting the positive electrode active material)

The third aspect of the present invention relates to the positive electrode active material for a nonaqueous electrolyte secondary battery according to the first and second aspects, wherein the organic phosphite compound is at least one compound selected from trimethyl phosphite or triethyl phosphite.

The fourth aspect of the present invention relates to the positive electrode active material for a nonaqueous electrolyte secondary battery according to the first and second aspects, wherein the organic phosphate compound is trimethyl phosphate.

The fifth aspect of the present invention relates to the positive electrode active material for a nonaqueous electrolyte secondary battery according to the first and second aspects, wherein an amount of phosphorus contained in the positive electrode active material is 0.10% by weight or less.

The sixth aspect of the present invention relates to the positive electrode active material for a nonaqueous electrolyte secondary battery according to the first and second aspects, wherein the adhesion to the surface of the positive electrode active material is based on chemical adsorption.

The seventh aspect of the present invention relates to the positive electrode active material for a nonaqueous electrolyte secondary battery according to the first and second aspects, wherein any one or more of a phosphate or polyphosphate compound represented by the following chemical formula (5), and a cyclic phosphate compound where both ends of a polyphosphate compound are bound to each other adhere to a part or the entire of the particle surface of the lithium-manganese-nickel composite oxide.

[Formula 5]

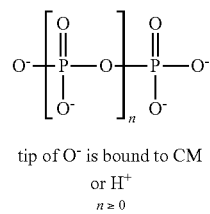

(5)

tip of O⁻ is bound to CM or H⁺

$n \geq 0$

The eighth aspect of the present invention relates to a method for producing the positive electrode active material for a nonaqueous electrolyte secondary battery according to the first to seventh aspects, the method including contacting a lithium-manganese-nickel composite oxide particle with an atmosphere gas including one or both of a volatile organic phosphite compound and a volatile organic phosphate compound, to allow one or both of the organic phosphite compound and the organic phosphate compound to adhere to a part or the entire of a surface of the lithium-manganese-nickel composite oxide particle.

The ninth aspect of the present invention relates to the method for producing the positive electrode active material for a nonaqueous electrolyte secondary battery according to the eighth aspect, wherein the atmosphere gas is an inert gas.

The tenth aspect of the present invention relates to the method for producing a positive electrode active material for a nonaqueous electrolyte secondary battery, the method including further heating the positive electrode active material for a nonaqueous electrolyte secondary battery obtained by the producing method according to the eighth and ninth aspects, at 100° C. to 700° C. in an oxidation atmosphere or a vacuum atmosphere.

The eleventh aspect of the present invention relates to a nonaqueous electrolyte secondary battery including a positive electrode, a negative electrode, a separator and a nonaqueous electrolyte, wherein
a positive electrode active material of the positive electrode is the positive electrode active material for a nonaqueous electrolyte secondary battery according to any one of the first to seventh aspects.

The present invention can provide a lithium-manganese-nickel composite oxide that imparts a high capacity and an excellent cycle characteristic when used as a positive electrode active material of a secondary battery.

In addition, the present invention can provide a producing method that can allow an organic phosphite compound and/or an organic phosphate compound to easily adhere to a lithium-manganese-nickel composite oxide in production on an industrial scale.

Furthermore, the present invention can provide a nonaqueous electrolyte secondary battery in which a lithium-manganese-nickel composite oxide that carries an organic phosphate is used as a positive electrode active material.

DETAILED DESCRIPTION

Figure 1:
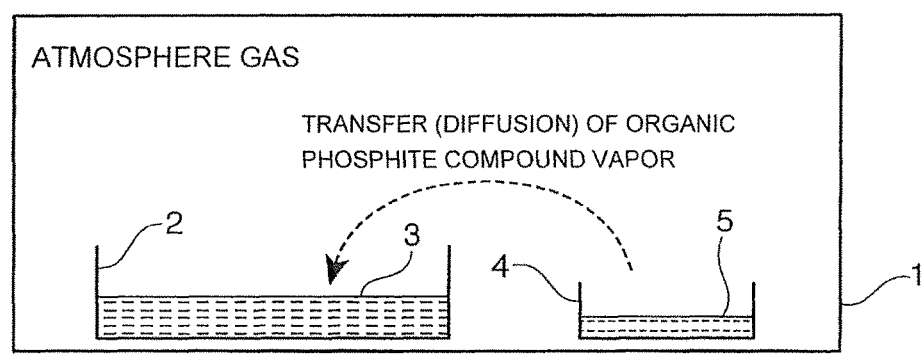
FIG. 1 is a schematic view illustrating one example of a surface treatment step in the present invention.

1. Positive Electrode Active Material for Nonaqueous Electrolyte Secondary Battery The positive electrode active material for a nonaqueous electrolyte secondary battery, of the present invention, (hereinafter, referred to as "positive electrode active material") is a lithium-manganese-nickel composite oxide particle in which the lithium-manganese-nickel composite oxide is represented by general formula: $Li_tMn_{2-x-y}Ni_xM_yO_4$ (wherein $0.96 < t \leq 1.25$, $0.40 \leq x \leq 0.60$, $0 \leq y \leq 0.20$, and M represents at least one element selected from Mg, Al, Si, Ti, Cr, Fe, Co, Cu and Zn) and any one or both of the organic phosphite compound of the chemical formula (1) and the organic phosphate compound of the chemical formula (2) adhere(s) to the surface of the lithium-manganese-nickel composite oxide particle.

The "adhesion" of the organic phosphite compound and/or the organic phosphate compound encompasses both of chemical adsorption with chemical interaction and physical adsorption due to a weak force such as van der Waals' force. In particular, chemical adsorption preferably imparts lithium-manganese-nickel oxide by itself, or any form thereof chemically reacted with other impurities or the like deposited on the surface, such as a form thereof hydrolyzed by water adsorbing onto the lithium-manganese-nickel composite oxide particle or a form thereof reacted with the unreacted lithium compound remaining at the time of lithium-manganese-nickel composite oxide synthesis.

Particularly preferably, a part or the entire of the organic phosphite compound or the organic phosphate compound carried on the positive electrode active material is sequentially subjected to oxidation, hydrolysis, and the like, converted to the phosphate diester compound represented by the chemical formula (3) or the phosphonate monoester compound represented by the chemical formula (4), and chemically bound to a constitutional element (CM) of the positive electrode active material. It is here considered that the phosphate diester and the phosphonate monoester each function as a weak acid and therefore serve to protect the positive electrode active material from the attack of hydrofluoric acid which causes metal elution in a battery.

Heating or the like can also remove an organic substance from the organic phosphite compound carried. Such removal is preferable for an application where an organic substance is not preferable, because a polyphosphate typified by phosphate, tripolyphosphate or the like (see the following formula (6)), and a cyclic polyphosphate typified by hexametaphosphate or the like (see the following formula (7)) are generated on the surface and can be chemically bound to a constitutional element (CM) of the positive electrode active material.

[Formula 6]

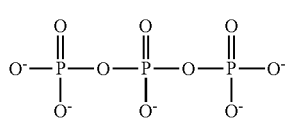

(6)

tip of O⁻ is bound to CM or H⁺

[Formula 7]

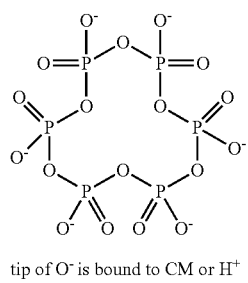

(7)

tip of O⁻ is bound to CM or H⁺

2. Lithium-Manganese-Nickel Composite Oxide Particle

The lithium-manganese-nickel composite oxide particle of the present invention is required to even singly exhibit excellent performance as a positive electrode active material, and is thus required to satisfy the following requirements.

The "t" value representing the content of lithium (Li) is more than 0.96 and 1.25 or less, preferably 0.98 or more and 1.20 or less, more preferably 1.00 or more and 1.20 or less.

The "t" value can be regulated in the above range to result in enhancements in output characteristics and capacity characteristics of a secondary battery in which the positive electrode active material is used.

On the contrary, if the "t" value is 0.96 or less, the positive electrode resistance of a secondary battery is increased, thereby making it impossible to improve output characteristics. On the other hand, if the "t" value exceeds 1.25, the initial discharging capacity is reduced due to the following: lithium by itself is a metal allowing no oxidation-reduction reaction to occur.

Nickel (Ni) is an element contributing to a higher potential and a higher capacity of a secondary battery.

The "x" value representing the amount of nickel to be added is 0.40 or more and 0.60 or less, preferably 0.40 or more and 0.56 or less, more preferably 0.40 or more and 0.50 or less.

If the "x" value is less than 0.40, a secondary battery in which the positive electrode active material is used is decreased in the battery capacity at a 5-V level. On the other hand, if the "x" value exceeds 0.60, a heterogeneous phase including much nickel is generated, thereby making it impossible to provide a positive electrode active material having desired properties.

The lithium-manganese-nickel composite oxide particle of the present invention may contain, in addition to the above-mentioned metal elements, an additive element M depending on the intended use and/or the required performance of a secondary battery.

Specifically, at least one element selected from magnesium (Mg), aluminum (Al), silicon (Si), titanium (Ti), chromium (Cr), iron (Fe), cobalt (Co), copper (Cu) and zinc (Zn) can be used as the additive element M.

The value representing the amount of the additive element M to be added is 0 or more and 0.20 or less, preferably 0 or more and 0.15 or less, more preferably 0 or more and 0.10 or less.

If the content of the additive element M exceeds 0.20, a metal element contributing to a Redox reaction is decreased, causing the problem of reduction in the battery capacity.

The lithium-manganese-nickel composite oxide particle of the present invention is characterized in that a group of peaks attributed to a diffraction pattern of a spinel type crystal structure with the space group Fd-3m is detected in a diffraction pattern obtained by evaluation with XRD.

The specific surface area (hereinafter, referred to as "BET specific surface area") of the lithium-manganese-nickel composite oxide particle of the present invention, measured by a BET method with nitrogen adsorption, is required to be controlled in the range from 0.7 $m^2/g$ to 1.5 $m^2/g$, preferably 0.8 $m^2/g$ to 1.2 $m^2/g$, more preferably 0.9 $m^2/g$ to 1.2 $m^2/g$.

Desorption and insertion of a lithium ion by the charging/discharging current of a secondary battery occur on the surface of the positive electrode active material. Therefore, if the BET specific surface area is less than 0.7 $m^2/g$, the contact area with the electrolytic solution is small and the positive electrode resistance is increased. On the other hand, if the BET specific surface area exceeds 1.5 $m^2/g$, a side reaction at the interface with the electrolytic solution occurs to thereby decompose the electrolytic solution, causing an increase in resistance.

The average particle size of the lithium-manganese-nickel composite oxide particle of the present invention is in the range from 2 μm to 8 μm, preferably 3 μm to 8 μm, more preferably 3 μm to 7 μm.

The average particle size here means the volume average particle size, and can be determined from the volume integrated value measured with, for example, a laser diffraction/scattering type particle size analyzer.

When the average particle size of the positive electrode active material is within such a range, the charging/discharging capacity and output characteristics of a secondary battery in which the positive electrode active material is used can be further enhanced. On the contrary, if the average particle size of the positive electrode active material is less than 2 μm, packing property of the positive electrode active material may be deteriorated to result in reduction in the charging/discharging capacity of a secondary battery to be obtained. On the other hand, if the average particle size of the positive electrode active material exceeds 8 μm, the BET specific surface area may be reduced to cause an increase in the positive electrode resistance.

3. Organic Phosphite Compound and Organic Phosphate Compound 3-1. Organic Phosphite Compound The organic phosphite compound for use in the present invention is represented by the following chemical formula (8).

In the formula, $R_1$, $R_2$ and $R_3$ each represent an organic functional group composed of an alkyl group, an aryl group, and the like, and specifically, at least one organic compound selected from tributyl phosphite, triethyl phosphite, trihexyl phosphite, triisodecyl phosphite, triisopropyl phosphite, trimethyl phosphite, trioctyl phosphite, triphenyl phosphite and the like is used therefor. Among them, trimethyl phosphite and triethyl phosphite high in volatility are preferably used for the reason associated with a producing method described below.

[Formula 8]

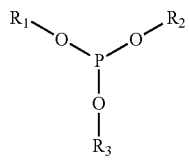

(8)

wherein $R_1$, $R_2$, and $R_3$ each represent an organic functional group composed of an alkyl group, an aryl group, and the like

3-2. Organic Phosphate Compound

The organic phosphate compound for use in the present invention is represented by the following chemical formula (9).

In the formula, $R_1$, $R_2$ and $R_3$ each represent an organic functional group composed of an alkyl group, an aryl group, and the like, and specifically, at least one organic compound selected from tributyl phosphate, triethyl phosphate, dibutyl phosphate, triallyl phosphate, triphenyl phosphate and the like is used therefor. Among them, trimethyl phosphate high in volatility is preferably used for the reason associated with a producing method described below.

[Formula 9]

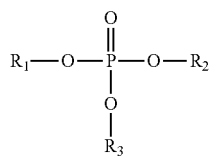

(9)

wherein $R_1$, $R_2$, and $R_3$ each represent an organic functional group composed of an alkyl group, an aryl group, and the like

3-3. Characteristics of Organic Phosphite Compound and Organic Phosphate Compound The organic phosphite compound or the organic phosphate compound is high in reactivity, and can form a uniform film on the surface of lithium-manganese-nickel oxide even when used in a small amount. The organic phosphite compound or the organic phosphate compound is preferably added to the lithium-manganese-nickel oxide so as to be in an amount of 0.10% by weight or less based on the amount of phosphorus, more preferably 0.01% by weight or more and 0.10% by weight or less.

Herein, a region where the amount of adsorption of the phosphate compound is smaller is higher in the battery capacity, and a region where the amount of the organic phosphite compound or the organic phosphate compound is larger is suppressed in elution of a metal ion from the lithium-manganese-nickel oxide, resulting in an excellent cycle characteristic of a battery.

4. Producing Method

4-1. Synthesis of Lithium-Manganese-Nickel Composite Oxide

Hereinafter, one example of a method for producing the lithium-manganese-nickel composite oxide is shown.

First, a plurality of metal compounds containing manganese is dissolved in water in a predetermined ratio to prepare a mixed aqueous solution. The compositional ratio of respective metals here is the same as the compositional ratio of a composite hydroxide particle to be finally obtained. Therefore, the mixed aqueous solution is prepared by modulating the ratio of the metal compounds to be dissolved in water so that the compositional ratio of respective metals in the mixed aqueous solution is the same as the compositional ratio of respective metals in the composite hydroxide particle of the present invention.

Next, water is placed in a reaction tank, and an aqueous sodium hydroxide solution and ammonia water are added in proper amounts to adjust the pH value in the reaction tank to be 11.2 to 12.2 on the basis of a liquid temperature of 25° C., and the ammonia concentration to 2 to 15 g/L.

A pH of less than 11.2 is not preferable because many impurities due to anions forming the metal compounds as raw materials are incorporated into the composite hydroxide particle. A pH of more than 12.2 is not preferable because the composite hydroxide particle is obtained in the form of a fine particle.

An ammonia concentration of less than 2 g/L is not preferable because the composite hydroxide particle does not have a spherical shape. An ammonia concentration of more than 15 g/L is not preferable because the solubility of nickel forming an ammonia complex is increased not to allow the composite hydroxide particle to achieve a target composition.

The atmosphere in the reaction tank is preferably a non-oxidizing atmosphere, and the oxygen concentration is preferably 1% by volume or less even if oxygen is contained. An oxygen concentration of more than 1% by volume is not preferable because manganese oxidized is precipitated as a fine particle.

The temperature of the reaction tank is set at 40 to 60° C., preferably 45 to 55° C.

The temperature of the reaction tank is naturally raised due to reaction heat and/or stirring energy, and therefore a temperature of less than 40° C. is not preferable because, if the temperature of the reaction tank is tried to be maintained at such a temperature, excessive energy is consumed by cooling. A temperature of more than 60° C. is not preferable because the amount of evaporation of ammonia is increased to hardly allow a target ammonia concentration to be maintained.

After adjustment of the reaction tank, the mixed aqueous solution is dropped into the reaction tank at a constant rate, to provide an aqueous reaction solution. Here, 25% by mass ammonia water and an aqueous 25% by mass sodium hydroxide solution are also dropped at constant rates, and the pH value of the aqueous reaction solution on the basis of a liquid temperature of 25° C. and the ammonia concentration are controlled so as to be maintained at 11.2 to 12.2 and 2 to 15 g/L, respectively, to thereby crystallize a manganese-nickel composite hydroxide particle (hereinafter, referred to as "composite hydroxide particle").

Thereafter, a slurry including the manganese-nickel composite hydroxide particle recovered through an overflow provided on the reaction tank is filtered and the resultant is dried to thereby provide a powdery manganese-nickel composite hydroxide particle.

A lithium compound is added to the resulting manganese-nickel composite hydroxide particle so that the content of lithium relative to the total number of atoms of metals contained in the particle is 46 to 62.5% by atom, and the resultant is mixed to thereby provide a lithium mixture.

The lithium compound is not particularly limited, and for example, lithium hydroxide, lithium nitride or lithium carbonate, or a mixture thereof can be used. In particular, lithium carbonate is preferably used in consideration of ease of handling and quality stability.

The resulting lithium mixture is fired at 800 to 1000° C. in the air for 5 to 24 hours, and cooled to room temperature to provide a lithium-manganese-nickel composite oxide.

A firing temperature of less than 800° C. is not preferable because the crystal structure of the lithium-manganese-nickel composite oxide is not sufficiently grown. A firing temperature of more than 1000° C. is not preferable because oxygen defects are generated.

A firing time of less than 5 hours is not preferable because the temperature in a firing vessel is partially ununiform. Firing for more than 24 hours is not preferable in terms of energy efficiency because a lithium-manganese-nickel composite oxide particle to be obtained is the same as that to be obtained in the case of firing for 24 hours.

If the lithium-manganese-nickel composite oxide is observed to be slightly sintered, it may be subjected to a grinding treatment.

4-2. Treatment of Lithium-Manganese-Nickel Composite Oxide Surface

Any method may be adopted as the method for producing the positive electrode active material of the present invention as long as it allows the organic phosphite compound and/or the organic phosphate compound to be uniformly dispersed on the lithium-manganese-nickel composite oxide surface to such an extent that elution of a metal ion can be suppressed.

For example, the organic phosphite compound and/or the organic phosphate compound, when being liquid(s), may be directly mixed with the lithium-manganese-nickel composite oxide, and when being solid(s), may be dissolved in an appropriate organic solvent and then mixed, or may be directly mixed in the form of solid(s). When an organic solvent is used, the organic solvent is preferably dried after mixing.

In order to allow small amount(s) of the organic phosphite compound and/or the organic phosphate compound to efficiently adhere to the lithium-manganese-nickel composite oxide, however, it is preferable to use a method including contacting the vapor of the volatile organic phosphite compound with a part or the entire of the surface of the lithium-manganese-nickel composite oxide particle, the method corresponding to the method for producing the positive electrode active material of the present invention.

The producing method is characterized in that, when the lithium-manganese-nickel composite oxide particle is made of a secondary particle formed by a primary particle agglomerate and any pore is present between primary particles, a uniform surface treatment layer at a nanometer (nm) level can also be formed on the surface of each primary particle with the pore interposed.

Hereinafter, the detail is described.

Figure 2:
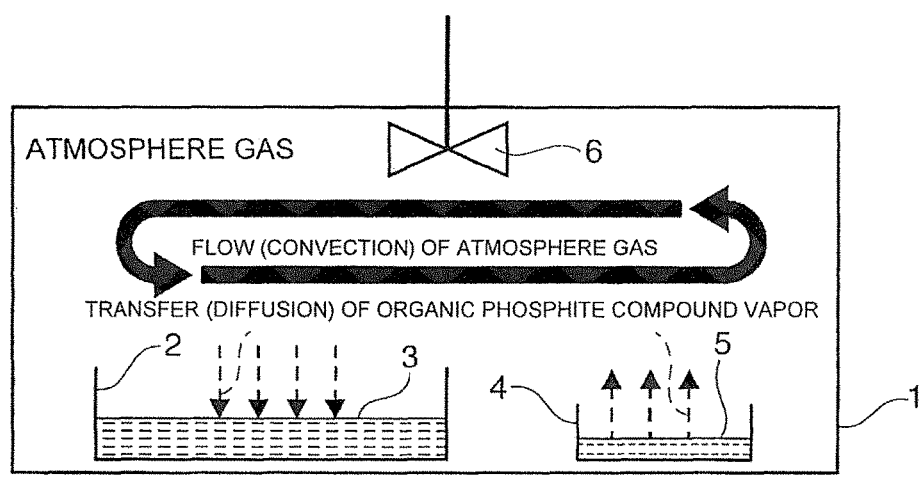
FIG. 2 is a schematic view illustrating one example of a surface treatment step in the present invention.

FIGS. 1 and 2 are each a schematic view illustrating one example of a surface treatment step. Herein, FIGS. 1 and 2 illustrate a case where the "organic phosphite compound" is used as the organic compound to be carried.

In FIG. 1 and FIG. 2, reference number 1 represents a reaction vessel, reference number 2 represents a receiving vessel, reference number 3 represents a lithium-manganese-nickel composite oxide particle, reference number 4 represents a receiving vessel of the organic volatile compound to be carried, reference number 5 represents a volatile organic phosphite compound or organic phosphate compound, and reference number 6 represents a fan. When the organic phosphate compound is used in the organic compound to be carried, the organic phosphate compound is prepared in the receiving vessel marked with reference number 4, and when both are used in the organic compound to be carried, a receiving vessel receiving the organic phosphite compound and a receiving vessel receiving the organic phosphate compound are prepared.

The surface treatment step is, for example, performed as follows: the receiving vessel 2 of the lithium-manganese-nickel composite oxide particle, and the receiving vessel 4 of the volatile organic phosphite compound or the organic phosphate compound are installed in the reaction vessel 1, as illustrated in FIG. 1, and predetermined amounts of the lithium-manganese-nickel composite oxide particle 3, and the volatile organic phosphite compound or organic phosphate compound 5 are placed in the respective receiving vessels, and the resultant is left to stand in an atmosphere gas.

The reaction vessel 1 is required to be a vessel high in sealability so as not to leak the atmosphere gas and any volatile acidic compound vapor to the outside, and examples of the material thereof include plastics such as polyethylene, polypropylene and Teflon (registered trademark), ceramics such as alumina, quartz and glass, and metals such as stainless steels (SUS304, SUS316, and the like) and titanium, but are not limited thereto as long as such materials are not reactive with the volatile organic phosphite compound vapor.

The receiving vessel 2 of the lithium-manganese-nickel composite oxide particle, and the receiving vessel 4 of the volatile organic phosphite compound or the organic phosphate compound are required to be non-reactive with the lithium-manganese-nickel composite oxide particle and the volatile organic phosphite compound or organic phosphate compound 5, and to have durability, examples of the material thereof include plastics such as polyethylene, polypropylene and Teflon (registered trademark), ceramics such as alumina, quartz and glass, and metals such as stainless steels and titanium, and such a material can be appropriately selected depending on the types of the lithium-manganese-nickel composite oxide particle and the volatile organic phosphite compound or organic phosphate compound 5 to be used.

The atmosphere gas is required to be non-reactive with the lithium-manganese-nickel composite oxide particle and the volatile organic phosphite compound or organic phosphate compound 5, examples thereof include nitrogen and argon, and such an atmosphere gas may be appropriately selected depending on the types of the lithium-manganese-nickel composite oxide particle and the volatile organic phosphite compound or organic phosphate compound 5 to be used.

Trimethyl phosphite is easily oxidized and thus converted to trimethyl phosphate low in volatility, if oxygen is contained in the atmosphere. Therefore, when trimethyl phosphite (trimethoxyphosphine) is used as the volatile organic phosphite compound in the surface treatment step, the atmosphere gas is preferably nitrogen or argon containing no oxygen.

In the reaction vessel 1, while the vapor of the volatile organic phosphite compound or organic phosphate compound 5 is diffused from the receiving vessel 4 of the volatile organic phosphite compound or the organic phosphate compound into the atmosphere gas, the vapor of the volatile organic phosphite compound or organic phosphate compound 5 diffused into the atmosphere gas adheres to the surface of the lithium-manganese-nickel composite oxide particle 3 in the receiving vessel 2 of the lithium-manganese-nickel composite oxide particle and is consumed, and therefore the volatile organic phosphite compound or organic phosphate compound 5 is mass-transferred from the inside of the receiving vessel 4 of the volatile organic phosphite compound or the organic phosphate compound to the receiving vessel 2 of the lithium-manganese-nickel composite oxide particle as the reaction time passes.

When the surface treatment step is performed, the atmosphere gas containing the vapor of the organic phosphite compound or organic phosphate compound 5 in the reaction vessel 1 may be forcedly convected by the fan 6 or the like, as illustrated in FIG. 2.

The reason for this is because the atmosphere gas can be convected to thereby allow the vapor of the organic phosphite compound or organic phosphate compound 5 to be mass-transferred from the inside of the receiving vessel 4 of the organic phosphite compound or organic phosphate compound to the lithium-manganese-nickel composite oxide particle (oxide particle 3) in a shorter time, thereby resulting in a significant reduction in the surface treatment time.

When the vapor pressure of the organic phosphite compound or organic phosphate compound is low, the organic phosphite compound or organic phosphate compound may also be volatilized by heating, under reduced pressure, or the like.

The positive electrode active material subjected to the surface treatment may be fired in an oxidation atmosphere or in vacuum under a temperature condition of 100° C. or more and 700° C. or less.

Such firing can remove organic substances including linear hydrocarbon and dry hydrocarbon carried on the positive electrode active material, and thus a surface without any organic components can be obtained. Therefore, the article of the present invention can also be used in an application where any organic component is not preferred.

A temperature in such firing of less than 100° C. is not preferable because such organic components cannot be sufficiently removed. In addition, heating at a temperature of more than 700° C. is not preferable because cycle characteristic is deteriorated. The reason why cycle characteristic is deteriorated is considered because aggregation of a phosphorus compound causes the effect of protecting the active material surface from the electrolytic solution to be lost. In addition, firing in a reductive atmosphere is not preferable because the positive electrode active material is reduced and thus partially converted into a metal. The term "oxidation atmosphere" refers to an atmosphere containing an oxidizing gas.

4-3. Nonaqueous Electrolyte Secondary Battery

The nonaqueous electrolyte secondary battery of the present invention includes a positive electrode, a negative electrode, a separator, a nonaqueous electrolytic solution, and the like, and is configured from the same components as in a common nonaqueous electrolyte secondary battery.

Embodiments described below are merely illustrative, and the nonaqueous electrolyte secondary battery of the present invention can be carried out in any mode where various modifications and alternations are made based on the knowledge of those skilled in the art with reference to embodiments described herein. The nonaqueous electrolyte secondary battery of the present invention is not particularly limited in terms of applications thereof.

(1) Positive Electrode

The positive electrode active material for a nonaqueous electrolyte secondary battery of the present invention is used to produce a positive electrode of a nonaqueous electrolyte secondary battery, for example, as follows.

First, a powdery positive electrode active material, a conductive material and a binder are mixed, activated carbon and a solvent for viscosity adjustment or the like are, if necessary, further added thereto, and the resultant is kneaded to produce a positive electrode mixture paste.

The mixing ratio of the respective components in the positive electrode mixture paste is appropriately selected depending on the application and the performance to be demanded of a secondary battery and is not particularly limited. When the solid content of the positive electrode mixture excluding the solvent is defined as 100 parts by mass, the content of the positive electrode active material is desirably 60 parts by mass to 95 parts by mass, the content of the conductive material is desirably 1 part by mass to 20 parts by mass and the content of the binder is desirably 1 part by mass to 20 parts by mass, as in the positive electrode of a common nonaqueous electrolyte secondary battery.

The resulting positive electrode mixture paste is applied onto the surface of a current collector made of aluminum foil, and dried to release the solvent. The resultant may also be, if necessary, pressurized by roll-pressing or the like for the purpose of an increase in the electrode density. A sheet-shaped positive electrode can be thus produced.

The sheet-shaped positive electrode can be cut to an appropriate size depending on the intended battery, and then subjected to producing of a battery. The method for producing the positive electrode, however, is not limited to the above example, and other method may be adopted.

In production of the positive electrode, for example, graphite (natural graphite, artificial graphite, expanded graphite, and the like) and a carbon black type material such as acetylene black and Ketjen black (registered trademark) can be used as the conductive material.

The binder serves to bind the active material particle, and for example, polyvinylidene fluoride (PVDF), polytetrafluoroethylene (PTFE), fluororubber, ethylene-propylene-diene rubber, styrene-butadiene, a cellulose type resin, and polyacrylic acid can be used.

If necessary, the positive electrode active material, the conductive material and the activated carbon are dispersed, and a solvent for dissolving the binder is added to the positive electrode mixture. Specifically, an organic solvent such as N-methyl-2-pyrrolidone can be used as the solvent. In addition, activated carbon can also be added to the positive electrode mixture for the purpose of an increase in the electric double layer capacity.

(2) Negative Electrode

As the negative electrode, a negative electrode can be used which is formed by mixing a binder with a metal lithium or a lithium alloy, or a negative electrode active material that can absorb and desorb a lithium ion, adding an appropriate solvent thereto to provide a paste-like negative electrode mixture, applying the negative electrode mixture onto the surface of a foil current collector made of a metal such as copper, drying the resultant, and if necessary compressing it for the purpose of an increase in the electrode density.

For example, a fired product of an organic compound such as natural graphite, artificial graphite and a phenol resin, and a powder of a carbon substance such as coke can be used as the negative electrode active material.

In such a case, a fluorine-containing resin such as PVDF can be used as the binder of the negative electrode, as in the positive electrode, and an organic solvent such as N-methyl-2-pyrrolidone can be used as a solvent for allowing the active material and the binder to be dispersed.

(3) Separator

The separator is interposed and disposed between the positive electrode and the negative electrode. The separator separates the positive electrode and the negative electrode and holds an electrolyte, and a film that is a thin film made of polyethylene, polypropylene or the like and that has many micropores can be used therefor.

(4) Nonaqueous Electrolytic Solution

The nonaqueous electrolytic solution is obtained by dissolving a lithium salt as a support salt in an organic solvent.

As the organic solvent, any one or more selected from cyclic carbonates such as ethylene carbonate, propylene carbonate, butylene carbonate and trifluoropropylene carbonate, linear carbonates such as diethyl carbonate, dimethyl carbonate, ethyl methyl carbonate and dipropyl carbonate, ether compounds such as tetrahydrofuran, 2-methyltetrahydrofuran and dimethoxyethane, sulfur compounds such as ethyl methyl sulfone and butanesultone, and phosphorus compounds such as triethyl phosphate and trioctyl phosphate can be used singly or as a mixture.

$LiPF_6$, $LiBF_4$, $LiClO_4$, $LiAsF_6$, $LiN(CF_3SO_2)_2$, and composite salts thereof can be used as the support salt.

The nonaqueous electrolytic solution may include a radical scavenger, a surfactant, a flame retardant, and the like in order to improve battery characteristics.

(5) Shape and Configuration of Battery

The nonaqueous electrolyte secondary battery of the present invention, including the positive electrode, the negative electrode, the separator and the nonaqueous electrolytic solution, as described above, can be formed into various shapes such as a cylindrical shape and a stacked shape.

No matter which shape is adopted, the nonaqueous electrolyte secondary battery is completed by stacking the positive electrode and the negative electrode with the separator interposed therebetween to provide an electrode body, impregnating the resulting electrode body with the nonaqueous electrolytic solution, connecting a positive electrode current collector and a positive electrode terminal in communication with the outside, and a negative electrode current collector and a negative electrode terminal in communication with the outside, by use of a current collection lead or the like, and enclosing the resultant in a battery case.

(6) Characteristics

The nonaqueous electrolyte secondary battery in which the positive electrode active material of the present invention is used has a high operating potential of 4.5 V or more, and also has a high capacity and is excellent in cycle characteristic.

Specifically, in the case where the positive electrode active material of the present invention is used in the positive electrode to form a coin battery including lithium foil as the negative electrode, and the coin battery is charged to a cut-off voltage of 5.0 V, paused for 1 hour and then discharged to a cut-off voltage of 3.0 V at a current density of 0.1 mA/cm$^2$ and at a measurement temperature of 25° C., an initial discharging capacity of 125 mAh/g or more, preferably 130 mAh/g or more is achieved.

In the case where a battery including, as the negative electrode, copper foil to which a graphite powder and polyvinylidene fluoride are applied, is formed, and subjected to conditioning where a cycle including charging to a cut-off voltage of 4.9 V, pausing for 1 hour and then discharging to a cut-off voltage of 3.5 V at a current density of 0.3 mA/cm$^2$ in a thermostat bath kept at 25° C. is repeated for 5 cycles and thereafter subjected to an operation where a cycle including charging to a cut-off voltage of 4.9 V, pausing for 1 hour and then discharging to a cut-off voltage of 3.5 V at a current density of 2.0 mA/cm$^2$ in a thermostat bath kept at 60° C. is repeated for 200 cycles, the capacity retention ratio, determined as the proportion obtained by dividing the discharge capacity obtained at the 200th cycle after conditioning by the discharge capacity obtained at the first cycle after conditioning, is 75% or more, preferably 80% or more.

(7) Application of Nonaqueous Electrolyte Secondary Battery

The nonaqueous electrolyte secondary battery of the present invention has the above characteristics, and therefore is suitable as a power source of small-sized mobile electronic equipment (a laptop computer, a mobile phone terminal, and the like) always demanded to have a high capacity. The nonaqueous electrolyte secondary battery of the present invention can also be smaller in size and higher in power, and therefore is also suitable as a power source for electric cars, which is restricted in terms of a mounting space.

The nonaqueous electrolyte secondary battery of the present invention can be used as not only a power source for electric cars which are driven purely by only electric energy, but also a power source for so-called hybrid cars in which electric energy is used in combination with a combustion engine such as a gasoline engine or a diesel engine.

EXAMPLES

Hereinafter, the present invention is specifically described with reference to Examples and Comparative Examples.

Example 1

[Production of Lithium-Manganese-Nickel Composite Oxide]

(a) Production of Precursor

First, water was placed in a reaction tank (5 L) in a half volume of the tank, and the temperature of water in the tank was set and kept at 50° C. with stirring.

The atmosphere in the reaction tank here was a nitrogen atmosphere (oxygen concentration: 1% by volume or less).

An aqueous 25% by mass sodium hydroxide solution and 25% by mass ammonia water were added in proper amounts to water in the reaction tank, to prepare a solution in the reaction tank so that the pH value in the reaction tank was 11.5 on the basis of a liquid temperature of 25° C. and the ammonia concentration was 5 g/L.

At the same time, manganese sulfate and nickel sulfate were dissolved in pure water so that the molar ratio of manganese and nickel satisfied Mn:Ni=1.50:0.50, thereby preparing an aqueous 2.0 mol/L raw material solution.

The aqueous raw material solution was dropped into the reaction tank at a constant rate, to provide an aqueous reaction solution. Here, 25% by mass ammonia water and an aqueous 25% by mass sodium hydroxide solution were also dropped at constant rates, and the pH value of the aqueous reaction solution on the basis of a liquid temperature of 25° C. and the ammonia concentration were controlled so as to be maintained at 11.5 and 5 g/L, respectively, to thereby crystallize a manganese-nickel composite hydroxide particle (hereinafter, referred to as "composite hydroxide particle").

Thereafter, a slurry including the composite hydroxide particle recovered through an overflow provided on the reaction tank was filtered and the resultant was dried to thereby provide a powdery composite hydroxide particle.

Lithium carbonate, which was weighted so that the content of lithium relative to the total number of atoms of manganese and nickel contained in the composite hydroxide particle thus obtained was 50% by atom, was added to the composite oxide particle, and the resultant was mixed by use of a Turbula shaker mixer (manufactured by Dalton Corporation, T2F) to thereby provide a lithium mixture.

(b) Firing Step

The resulting lithium mixture was fired by use of an atmosphere firing furnace (manufactured by Hirochiku Co., Ltd., HAF-2020S) in the air at 900° C. for 12 hours, and thereafter cooled to room temperature to provide a lithium-manganese-nickel composite oxide. The lithium-manganese-nickel composite oxide was observed to be slightly sintered, and therefore ground by use of a hammer mill (manufactured by IKA, MF10).

[Evaluation of Lithium-Manganese-Nickel Composite Oxide]

The lithium-manganese-nickel composite oxide thus obtained was evaluated as follows.

(a) Composition

It was confirmed by analysis with an ICP emission spectroscopic analyzer (manufactured by Varian Medical Systems, Inc., 725ES) that the positive electrode active material was represented by general formula: $LiMn_{1.50}Ni_{0.50}O_4$.

(b) Crystal Structure

The crystal structure of the positive electrode active material was observed with XRD (manufactured by PANalytical B.V., X'Pert, PROMRD), and a group of peaks of a spinel type crystal structure with the space group Fd-3m was thus detected.

(c) BET Specific Surface Area, Average Particle Size

The BET specific surface area of the positive electrode active material was measured with a fully automatic BET specific surface area measurement apparatus (manufactured by Mountech Co., Ltd., Macsorb), and was thus confirmed to be 1.25 $m^2/g$.

In addition, the average particle size on a volume basis was determined with a laser diffraction/scattering type particle size distribution measuring apparatus (manufactured by Nikkiso Co., Ltd., Microtrac HRA), and was thus confirmed to be 5.05 μm.

[Surface Treatment of Lithium-Manganese-Nickel Composite Oxide (Production of Positive Electrode Active Material)]

The lithium-manganese-nickel composite oxide produced in the above section, and trimethyl phosphite as the volatile organic phosphite compound were placed in a glass reactor having a volume of 1.0 L, as illustrated in FIG. 2, so that the weight ratio of the lithium-manganese-nickel composite oxide and trimethyl phosphite was 1.0000:0.0200, and a nitrogen gas was packed as the atmosphere gas. Thereafter, the resultant was left to stand for 30 hours with the content of the reactor being stirred by a fan, and trimethyl phosphite was allowed to adhere to the lithium-manganese-nickel composite oxide to produce a positive electrode active material. After a lapse of 30 hours, 59.7% of trimethyl phosphite was volatilized.

[Evaluation of Amount of Phosphorus Contained in Positive Electrode Active Material]

The positive electrode active material where trimethyl phosphite was allowed to adhere to the lithium-manganese-nickel composite oxide was subjected to analysis with an ICP emission spectroscopic analyzer (manufactured by Varian Medical Systems, Inc., 725ES), and it was thus found that the amount of phosphorus contained was 0.10% by weight.

The results are shown in Table 1.

[Evaluation of State of Phosphorus Compound Adhering to Positive Electrode Active Material Surface]

The positive electrode active material where trimethyl phosphite was allowed to adhere to the lithium-manganese-nickel composite oxide was subjected to measurement according to time of flight secondary ion mass spectrometry (TOF-SIMS) (manufactured by ULVAC-PHI, Inc., TRIFTV nanoTOF).

$C_2H_6O_4P$ having a molecular weight of 125 and $CH_4O_3P$ having a molecular weight of 95 are presumed as phosphorus-containing secondary ions to be observed on the mass spectrum, and, when represented by structural formulae, correspond to chemical formula (3) and chemical formula (4), respectively.

[Production of Secondary Battery]

A 2032 type coin battery (hereinafter, referred to as "coin type battery") was used for evaluation of the resulting positive electrode active material.

Figure 3:
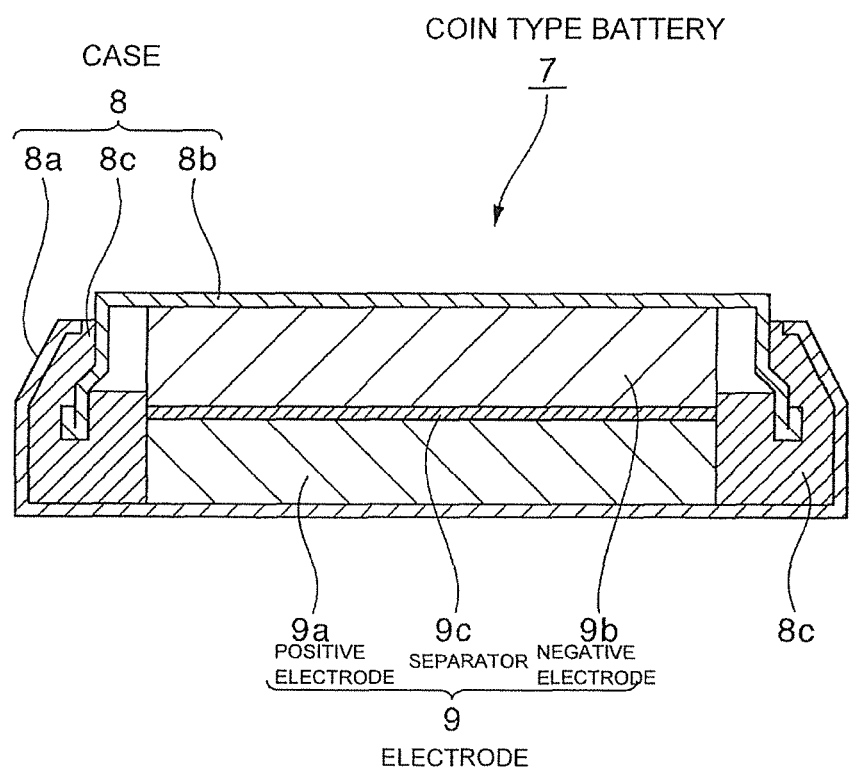
FIG. 3 is a schematic cross-sectional view of a 2032 type coin battery used for battery evaluation.

FIG. 3 is a schematic cross-sectional view of a 2032 type coin battery 7 used for battery evaluation, reference number 7 represents a 2032 type coin battery, reference number 8 represents a case, reference number 8a represents a positive electrode can, reference number 8b represents a negative electrode can, reference number 8c represents a gasket, reference number 9 represents an electrode, reference number 9a represents a positive electrode, reference number 9b represents a negative electrode, and reference number 9c represents a separator.

As illustrated in FIG. 3, the coin type battery 7 is configured from a case 8, and an electrode 9 received in the case 8.

The case 8 includes a hollow positive electrode can 8a opened at one end thereof, and a negative electrode can 8b disposed at the opening of the positive electrode can 8a, and is configured so that, when the negative electrode can 8b is disposed at the opening of the positive electrode can 8a, the electrode 9 is received between the negative electrode can 8b and the positive electrode can 8a.

The electrode 9 includes a positive electrode 9a, a separator 9c and a negative electrode 9b which are stacked so as to be arranged in this order, and is received in the case 8 so that the positive electrode 9a is in contact with the inner surface of the positive electrode can 8a and the negative electrode 9b is in contact with the inner surface of the negative electrode can 8b.

The case 8 is provided with a gasket 8c, and the gasket 8c allows the positive electrode can 8a and the negative electrode can 8b to be relatively movably secured so as to be kept in non-contact with each other. The gasket 8c also has a function of sealing the gap between the positive electrode can 8a and the negative electrode can 8b to air-tightly and liquid-tightly block the inside of the case 8 from the outside.

Such a coin type battery 7 was produced as follows.

First, 52.5 mg of the resulting positive electrode active material, 15 mg of acetylene black and 7.5 mg of a polytetrafluoroethylene resin (PTFE) were mixed, the mixture was formed into a thin film so that the film had a diameter of 10 mm and a weight of about 10 mg, to produce positive electrode 9a, and the positive electrode was dried in a vacuum dryer at 120° C. for 12 hours.

Next, the positive electrode 9a was used to produce the coin type battery 7 in a glove box in an Ar atmosphere, in which the dew point was controlled at −80° C.

Here, lithium foil punched into a disk shape having a diameter of 14 mm, or a negative electrode sheet in which a graphite powder having an average particle size of about 20 μm and polyvinylidene fluoride were applied onto copper foil was used as the negative electrode 9b.

A porous polyethylene film having a thickness of 25 μm was used as the separator 9c, and a 3:7 mixed liquid (produced by Tomiyama Pure Chemical Industries, Ltd.) of ethylene carbonate (EC) and diethyl carbonate (DEC), in which 1 M $LiPF_6$ was adopted as a support electrolyte, was used as the electrolytic solution.

[Evaluation of Secondary Battery]

The initial discharging capacity and the cycle characteristic exhibiting performances of the coin type battery 7 were evaluated as follows.

(a) Initial Discharging Capacity

The initial discharging capacity was evaluated by using lithium foil as the negative electrode to produce coin type battery 7 according to Example 1, thereafter leaving the coin type battery to stand in a thermostat bath kept at 25° C. for about 24 hours to stabilize the open circuit voltage OCV, and thereafter measuring the capacity (initial discharging capacity) in charging to a cut-off voltage of 5.0 V, pausing for 1 hour and then discharging to a cut-off voltage of 3.0 V at a current density of the positive electrode of 0.1 $mA/cm^2$.

As a result, the initial discharging capacity of coin type battery 7 of Example 1 was 127 mAh/g.

The results are shown in Table 1.

(b) Cycle Characteristic

The cycle characteristic was evaluated by measuring the capacity retention ratio in charging/discharging for 200 cycles.

Specifically, such evaluation was performed as follows: coin type battery 1 produced by using a sheet in which a graphite powder and polyvinylidene fluoride were applied to copper foil, as the negative electrode, was subjected to conditioning where a cycle including charging to a cut-off voltage of 4.9 V, pausing for 1 hour and then discharging to a cut-off voltage of 3.5 V at a current density of 0.3 $mA/cm^2$ in a thermostat bath kept at 25° C. was repeated for 5 cycles, and thereafter subjected to an operation where a cycle including charging to a cut-off voltage of 4.9 V, pausing for 1 hour and then discharging to a cut-off voltage of 3.5 V at a current density of 2.0 $mA/cm^2$ in a thermostat bath kept at 60° C. was repeated for 200 cycles, and the discharge capacity at each cycle was measured.

As a result, the capacity retention ratio of the coin type battery of Example 1, as the proportion obtained by dividing the discharge capacity obtained at the 200th cycle after conditioning by the discharge capacity obtained at the first cycle after conditioning, was 81%.

The results are shown in Table 1.

Example 2

A positive electrode active material according to Example 2 was produced under the same conditions as in Example 1 except that the standing time in adhesion of trimethyl phosphite to the lithium-manganese-nickel composite oxide was 24 hours.

The amount of phosphorus in the positive electrode active material and the battery evaluation results are shown in Table 1.

The state of the phosphorus compound was analyzed by TOF-SIMS, and peaks of $C_2H_6O_4P$ having a molecular weight of 125 and $CH_4O_3P$ having a molecular weight of 95 were observed.

Example 3

A positive electrode active material according to Example 3 was produced under the same conditions as in Example 2 except that the weight ratio of the lithium-manganese-nickel composite oxide and trimethyl phosphite was 1.0000: 0.0100.

The amount of phosphorus in the positive electrode active material and the battery evaluation results are shown in Table 1.

The state of the phosphorus compound was analyzed by TOF-SIMS, and peaks of $C_2H_6O_4P$ having a molecular weight of 125 and $CH_4O_3P$ having a molecular weight of 95 were observed.

Example 4

A positive electrode active material according to Example 4 was produced under the same conditions as in Example 2 except that the weight ratio of the lithium-manganese-nickel composite oxide and trimethyl phosphite was 1.0000: 0.0050.

The amount of phosphorus in the positive electrode active material and the battery evaluation results are shown in Table 1.

The state of the phosphorus compound was analyzed by TOF-SIMS, and peaks of $C_2H_6O_4P$ having a molecular weight of 125 and $CH_4O_3P$ having a molecular weight of 95 were observed.

Example 5

A positive electrode active material according to Example 5 was produced under the same conditions as in Example 2 except that the weight ratio of the lithium-manganese-nickel composite oxide and trimethyl phosphite was 1.0000: 0.0025.

The amount of phosphorus in the positive electrode active material and the battery evaluation results are shown in Table 1.

The state of the phosphorus compound was analyzed by TOF-SIMS, and peaks of $C_2H_6O_4P$ having a molecular weight of 125 and $CH_4O_3P$ having a molecular weight of 95 were observed.

Example 6

A positive electrode active material according to Example 6 was produced under the same conditions as in Example 2 except that the weight ratio of the lithium-manganese-nickel composite oxide and trimethyl phosphite was 1.0000: 0.0010.

The amount of phosphorus in the positive electrode active material and the battery evaluation results are shown in Table 1.

The state of the phosphorus compound was analyzed by TOF-SIMS, and peaks of $C_2H_6O_4P$ having a molecular weight of 125 and $CH_4O_3P$ having a molecular weight of 95 were observed.

Example 7

A positive electrode active material according to Example 7 was produced under the same conditions as in Example 2 except that the standing time in adhesion of trimethyl phosphite to the lithium-manganese-nickel composite oxide was 48 hours.

The amount of phosphorus in the positive electrode active material and the battery evaluation results are shown in Table 1.

The state of the phosphorus compound was analyzed by TOF-SIMS, and peaks of $C_2H_6O_4P$ having a molecular weight of 125 and $CH_4O_3P$ having a molecular weight of 95 were observed.

Example 8

A positive electrode active material according to Example 8 was produced under the same conditions as in Example 2 except that the organic phosphite compound was triethyl phosphite, the weight ratio of the lithium-manganese-nickel composite oxide and triethyl phosphite was 0.0134, and the standing time in adhesion of triethyl phosphite to the lithium-manganese-nickel composite oxide was 84 hours.

The amount of phosphorus in the positive electrode active material and the battery evaluation results are shown in Table 1.

Example 9

A positive electrode active material according to Example 9 was produced under the same conditions as in Example 2 except that the organic phosphate compound was trimethyl phosphate, the weight ratio of the lithium-manganese-nickel composite oxide and trimethyl phosphate was 0.0056, and the standing time in adhesion of trimethyl phosphate to the lithium-manganese-nickel composite oxide was 96 hours.

The amount of phosphorus in the positive electrode active material and the battery evaluation results are shown in Table 1.

Example 10

A positive electrode active material according to Example 10 was produced by heating the positive electrode active material obtained in Example 3 at 100° C. in the air.

The amount of phosphorus in the positive electrode active material and the battery evaluation results are shown in Table 1.

The state of the phosphorus compound was analyzed by TOF-SIMS, and peaks of $PO_3$ having a molecular weight of 79 and $PO_2$ having a molecular weight of 63 were observed. These peaks exhibited the presence of polyphosphate.

Example 11

A positive electrode active material according to Example 11 was produced by heating the positive electrode active material obtained in Example 3 at 300° C. in the air.

The amount of phosphorus in the positive electrode active material and the battery evaluation results are shown in Table 1.

The state of the phosphorus compound was analyzed by TOF-SIMS, and peaks of $PO_3$ having a molecular weight of 79 and $PO_2$ having a molecular weight of 63 were observed. These peaks exhibited the presence of polyphosphate.

Example 12

A positive electrode active material according to Example 12 was produced by heating the positive electrode active material obtained in Example 3 at 500° C. in the air.

The amount of phosphorus in the positive electrode active material and the battery evaluation results are shown in Table 1.

The state of the phosphorus compound was analyzed by TOF-SIMS, and peaks of $PO_3$ having a molecular weight of 79 and $PO_2$ having a molecular weight of 63 were observed. These peaks exhibited the presence of a phosphate compound or a polyphosphate compound.

Example 13

A positive electrode active material according to Example 13 was produced by heating the positive electrode active material obtained in Example 3 at 700° C. in the air.

The amount of phosphorus in the positive electrode active material and the battery evaluation results are shown in Table 1.

The state of the phosphorus compound was analyzed by TOF-SIMS, and peaks of $PO_3$ having a molecular weight of 79 and $PO_2$ having a molecular weight of 63 were observed. These peaks exhibited the presence of a phosphate compound or a polyphosphate compound.

Example 14

A positive electrode active material according to Example 14 was produced by heating the positive electrode active material obtained in Example 3 at 100° C. in vacuum.

The amount of phosphorus in the positive electrode active material and the battery evaluation results are shown in Table 1.

The state of the phosphorus compound was analyzed by TOF-SIMS, and peaks of $PO_3$ having a molecular weight of 79 and $PO_2$ having a molecular weight of 63 were observed. These peaks exhibited the presence of a phosphate compound or a polyphosphate compound.

Comparative Example 1

A lithium-manganese-nickel composite oxide that carried neither an organic phosphite compound nor an organic phosphate compound was used as it was, as a positive electrode active material according to Comparative Example 1.

The battery evaluation results in Comparative Example 1 are shown in Table 1.

TABLE 1

| | | Surface treatment step | | | | Heat treatment step | | Battery evaluation results | |
|---|---|---|---|---|---|---|---|---|---|
| | Phosphorus compound | Weight ratio of phosphorus compound/ LMNO | Treatment time [h] | Volatilization ratio of TMP [%] | Amount of phosphorus in LMNO [wt %] | Temperature [C.°] | Atmosphere | Initial discharging capacity [mAh/g] | Capacity retention ratio [%] |
| Example 1 | Trimethyl phosphite | 0.0200 | 30 | 59.7 | 0.10 | None | None | 127 | 81 |
| Example 2 | Trimethyl phosphite | 0.0200 | 24 | 52.9 | 0.09 | None | None | 130 | 80 |
| Example 3 | Trimethyl phosphite | 0.0100 | 24 | 68.3 | 0.08 | None | None | 130 | 82 |
| Example 4 | Trimethyl phosphite | 0.0050 | 24 | 85.5 | 0.06 | None | None | 133 | 80 |
| Example 5 | Trimethyl phosphite | 0.0025 | 24 | 96.0 | 0.03 | None | None | 135 | 80 |
| Example 6 | Trimethyl phosphite | 0.0010 | 24 | 95.6 | 0.01 | None | None | 135 | 77 |
| Example 7 | Trimethyl phosphite | 0.0200 | 48 | 75.1 | 0.11 | None | None | 121 | 80 |
| Example 8 | Triethyl phosphite | 0.0134 | 84 | 76.5 | 0.08 | None | None | 130 | 82 |
| Example 9 | Trimethyl phosphate | 0.0056 | 96 | 86.4 | 0.04 | None | None | 132 | 80 |
| Example 10 | Trimethyl phosphite | 0.0100 | 24 | 68.3 | 0.08 | 100 | Air | 130 | 80 |
| Example 11 | Trimethyl phosphite | 0.0100 | 24 | 68.3 | 0.08 | 300 | Air | 130 | 80 |
| Example 12 | Trimethyl phosphite | 0.0100 | 24 | 68.3 | 0.08 | 500 | Air | 130 | 80 |
| Example 13 | Trimethyl phosphite | 0.0100 | 24 | 68.3 | 0.08 | 700 | Air | 130 | 78 |
| Example 14 | Trimethyl phosphite | 0.0100 | 24 | 68.3 | 0.08 | 100 | Vacuum | 130 | 80 |
| Comparative Example 1 | None | — | — | — | — | — | — | 135 | 71 |

It was found from Table 1 that the same capacity as the initial capacity was achieved and an excellent cycle characteristic represented by the capacity retention ratio was also achieved in Examples 1 to 9 according to the present invention as compared with Comparative Example 1 in which a lithium-manganese-nickel composite oxide particle not carrying any phosphate compound being an organic substance was used as the positive electrode active material.

It was also found that the organic substance could be removed from the surface of the positive electrode active material obtained by further heat-treating the produced positive electrode active material, of each of Examples 10 to 14 according to the present invention, with the initial capacity and the cycle characteristic (see "Capacity retention ratio") being kept.

REFERENCE SIGNS LIST

1 reaction vessel
2 receiving vessel
3 lithium-manganese-nickel composite oxide particle
4 receiving vessel of volatile organic phosphite compound or organic phosphate compound
5 volatile organic phosphite compound or organic phosphate compound
6 fan
7 2032 type coin battery
8 case
8a positive electrode can
8b negative electrode can
8c gasket
9 electrode
9a positive electrode
9b negative electrode
9c separator

The invention claimed is:

1. A positive electrode active material for a nonaqueous electrolyte secondary battery, wherein one or both of an organic phosphite compound represented by the following chemical formula (1) and an organic phosphate compound represented by the following chemical formula (2) adhere(s) to a part or an entire of a particle surface of a lithium-manganese-nickel composite oxide represented by general formula: $Li_tMn_{2-x-y}Ni_xM_yO_4$ (wherein $0.96<t\leq1.25$, $0.40\leq x\leq0.60$, $0\leq y\leq0.20$, and M represents at least one element selected from Mg, Al, Si, Ti, Cr, Fe, Co, Cu and Zn).

[Formula 1]

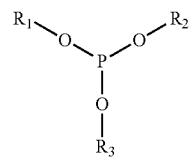

wherein $R_1$, $R_2$, and $R_3$ each represent an organic functional group including an alkyl group, an aryl group

[Formula 2]

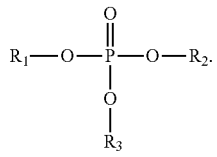

wherein $R_1$, $R_2$, and $R_3$ each represent an organic functional group including an alkyl group, an aryl group 2. The positive electrode active material for a nonaqueous electrolyte secondary battery according to claim 1, wherein, when the organic phosphite compound or the organic phosphate compound adheres to a surface of the positive electrode active material, a part or an entire of the organic phosphite compound or the organic phosphate compound chemically changed after adhesion of the organic phosphite compound or the organic phosphate compound is chemically bound to a component of the positive electrode active material in a form of a phosphate diester compound represented by the following chemical formula (3) or a phosphonate monoester compound represented by the following chemical formula (4).

[Formula 3]

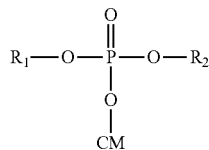

(3)

wherein $R_1$ and $R_2$ each represent an organic functional group including an alkyl group, an aryl group
(CM represents an element constituting the positive electrode active material)

[Formula 4]

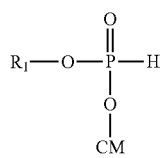

(4)

wherein $R_1$ represents an organic functional group including an alkyl group, an aryl group, and the like
(CM represents an element constituting the positive electrode active material)

3. The positive electrode active material for a nonaqueous electrolyte secondary battery according to claim 2, wherein the organic phosphite compound is at least one compound selected from trimethyl phosphite and triethyl phosphite.

4. The positive electrode active material for a nonaqueous electrolyte secondary battery according to claim 2, wherein the organic phosphate compound is trimethyl phosphate.

5. The positive electrode active material for a nonaqueous electrolyte secondary battery according to claim 2, wherein an amount of phosphorus contained in the positive electrode active material is 0.10% by weight or less.

6. The positive electrode active material for a nonaqueous electrolyte secondary battery according to claim 2, wherein the adhesion to the surface of the positive electrode active material is based on chemical adsorption.

7. The positive electrode active material for a nonaqueous electrolyte secondary battery according to claim 2, wherein any one or more of a phosphate or polyphosphate compound represented by the following chemical formula (5), and a cyclic phosphate compound where both ends of a polyphosphate compound are bound to each other adheres to a part or the entire of the particle surface of the lithium-manganese-nickel composite oxide.

[Formula 5]

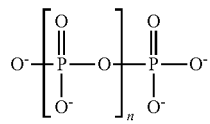

(5)

tip of O⁻ is bound to CM or H⁺
$n \geq 0$

8. A method for producing the positive electrode active material for a nonaqueous electrolyte secondary battery according to claim 1, the method comprising
contacting a lithium-manganese-nickel composite oxide particle with an atmosphere gas including one or both of a volatile organic phosphite compound and a volatile organic phosphate compound, to allow one or both of the organic phosphite compound and the organic phosphate compound to adhere to a part or an entire of a surface of the lithium-manganese-nickel composite oxide particle.

9. The method for producing the positive electrode active material for a nonaqueous electrolyte secondary battery according to claim 8, wherein the atmosphere gas is an inert gas.

10. The method for producing a positive electrode active material for a nonaqueous electrolyte secondary battery according to claim 8, the method comprising further heating the positive electrode active material, at 100° C. to 700° C. in an oxidation atmosphere or a vacuum atmosphere.

11. A nonaqueous electrolyte secondary battery comprising a positive electrode, a negative electrode, a separator and a nonaqueous electrolyte, wherein
a positive electrode active material of the positive electrode is the positive electrode active material for a nonaqueous electrolyte secondary battery according to any one of claim 1.

12. The positive electrode active material for a nonaqueous electrolyte secondary battery according to claim 1, wherein the organic phosphite compound is at least one compound selected from trimethyl phosphite or triethyl phosphite.

13. The positive electrode active material for a nonaqueous electrolyte secondary battery according to claim 1, wherein the organic phosphate compound is trimethyl phosphate.

14. The positive electrode active material for a nonaqueous electrolyte secondary battery according to claim 1, wherein an amount of phosphorus contained in the positive electrode active material is 0.10% by weight or less.

15. The positive electrode active material for a nonaqueous electrolyte secondary battery according to claim 1, wherein the adhesion to the surface of the positive electrode active material is based on chemical adsorption.

16. The positive electrode active material for a nonaqueous electrolyte secondary battery according to claim 1, wherein any one or more of a phosphate or polyphosphate compound represented by the following chemical formula (5), and a cyclic phosphate compound where both ends of a

[Formula 5]
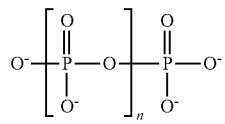
tip of O⁻ is bound to CM or H⁺
$n \geq 0$
polyphosphate compound are bound to each other adheres to a part or the entire of the particle surface of the lithium-manganese-nickel composite oxide.
* * * * *